(12) United States Patent
Hastings et al.

(10) Patent No.: US 8,649,864 B2
(45) Date of Patent: Feb. 11, 2014

(54) IMPLANTABLE HEART STIMULATOR PROVIDING LONG TERM CARDIAC MONITORING WITH AUTOMATIC NOTIFICATION

(75) Inventors: David F. Hastings, Lake Oswego, OR (US); Xin Good, Tigard, OR (US); Volker Lang, West Linn, OR (US)

(73) Assignee: Biotronik CRM Patent AG, Baar (CH)

( * ) Notice: Subject to any disclaimer, the term of this patent is extended or adjusted under 35 U.S.C. 154(b) by 1883 days.

(21) Appl. No.: 11/873,292

(22) Filed: Oct. 16, 2007

(65) Prior Publication Data

US 2009/0099617 A1    Apr. 16, 2009

(51) Int. Cl.
*A61N 1/365* (2006.01)

(52) U.S. Cl.
USPC ................................ 607/18; 600/300; 607/17

(58) Field of Classification Search
USPC ....................................... 600/300; 607/17–18
See application file for complete search history.

(56) References Cited

U.S. PATENT DOCUMENTS

| 6,263,243 | B1 | 7/2001 | Lang |
| 6,434,429 | B1 | 8/2002 | Kraus et al. |
| 6,470,215 | B1 | 10/2002 | Kraus et al. |
| 6,544,171 | B2 | 4/2003 | Beetz et al. |
| 6,553,262 | B1 | 4/2003 | Lang et al. |
| 6,934,585 | B1 * | 8/2005 | Schloss et al. ................ 607/9 |
| 2002/0193689 | A1 * | 12/2002 | Bernstein et al. ............ 600/454 |
| 2003/0028183 | A1 * | 2/2003 | Sanchez et al. ................ 606/34 |
| 2004/0049235 | A1 * | 3/2004 | Deno et al. ....................... 607/9 |
| 2005/0182447 | A1 * | 8/2005 | Schecter ........................... 607/2 |
| 2005/0240233 | A1 * | 10/2005 | Lippert et al. .................. 607/6 |
| 2007/0055170 | A1 * | 3/2007 | Lippert et al. ............... 600/547 |

* cited by examiner

*Primary Examiner* — Carl H Layno
*Assistant Examiner* — Jennifer Ghand
(74) *Attorney, Agent, or Firm* — ARC IP Law, PC; Joseph J. Mayo (57) ABSTRACT

An implantable medical device that continuously measures the patient's intracardiac ventricular impedance. Extracts cardiac performance information based on the intracardiac impedance, including amplitude, timing and variability of cardiac contraction function. The device records and analysis trends in the performance information. The device identifies changes, which exceed the selected threshold limits. In the event of an incipient crisis, the device transmits an alert message.

47 Claims, 3 Drawing Sheets

IMPLANTABLE HEART STIMULATOR PROVIDING LONG TERM CARDIAC MONITORING WITH AUTOMATIC NOTIFICATION

BACKGROUND OF THE INVENTION

1. Field of the Invention

The invention relates to implantable heart stimulators such as implantable cardiac pacemakers or implantable cardioverters/defibrillators (ICDs). In particular, the invention refers to implantable heart stimulators that comprise means for intracardiac impedance monitoring and for wireless transmission of data.

2. Description of the Related Art

Implantable medical devices comprising a telemetry unit for data communication with an external device allow for a data exchange between the implantable medical device and a central service center via the external device. Thus, the implantable medical device (implantable pacemaker or ICD) can transmit its operation parameters and physiological parameters measured e.g. by intracardiac or epicardial electrodes to the central service center where the data can be evaluated and a physician can be informed in case of any event needing a physician's assistance. By means of a wireless data transmission from the implantable medical device via the external device to the central service center a continuous monitoring of a patient is possible without the need for time consuming visits at the physician's premises.

Systems for such remote monitoring of patients are for example disclosed in U.S. Pat. No. 6,434,429, U.S. Pat. No. 6,470,215, U.S. Pat. No. 6,544,171 and U.S. Pat. No. 6,553,262.

The parameters to be monitored include a patient's heart rhythm, preferably both the atrial rhythm and the ventricular rhythm, the patients physical activity by means of hemodynamic sensor, therapeutic events such as atrial or ventricular stimulation pulses or defibrillation shocks triggered by the implantable medical device and intracardiac impedance.

It is also known to use intracardiac impedance for controlling the stimulation rate in a close loop stimulation system (CLS) as it is disclosed in U.S. Pat. No. 6,263,243.

BRIEF SUMMARY OF THE INVENTION

During the management of cardiovascular health and disease, a patient usually is outside of a clinical setting. When a cardiovascular system is challenged, it is susceptible to instabilities in rhythm and perfusion. Most of these challenges occur outside of a clinical setting. In particular while managing congestive heart failure or the recovery from myocardial infarcts, it is desirable to closely monitor the cardiovascular system and to identify conditions or combination of conditions, which may need to be corrected prior to their triggering of a medical emergency. While the patient is outside the clinical setting there is little information available on cardiovascular performance or acute vascular events. The missing information includes the efficacy of the therapy, and the patient's compliance to the therapeutic regimen version. There are no cost effective means for quantitative long term patient management or for providing timely alerts to acute vascular events.

It is an object of the invention to provide for an implantable heart stimulator offering improved remote monitoring for quantitative long term patient management.

According to the invention this object is achieved by an implantable heart stimulator comprising at least one stimulation pulse generator, at least one sensing unit, at least one impedance measuring unit, a hemodynamic sensor, a memory, a telemetry unit and a control unit. The at least one stimulation pulse generator is either connected to electrodes or connectors for such electrodes for intracardiac placement and is adapted to selectively generate a stimulation pulse for delivery to at least one chamber, e.g. the right ventricle of the heart when triggered by the control unit. The at least one sensing unit is also connected to electrodes of connectors for such electrodes for intracardiac placement and is adapted to process electric potentials that can be picked up by such intracardiac electrode in at least one chamber of the heart, e.g. the right ventricle to thus acquire an intracardiac electrocardiogram (IEGM). The at least one impedance measuring unit also is connected to at least one electrode or one connector for an electrode for intracardiac placement and is adapted to determine a unipolar ventricular impedance or conducting signal having a magnitude corresponding to the intracardiac impedance of at least one ventricle of the heart.

It is to be noted that instead of measuring impedance, conductance can be measured and evaluated taking into account the conductance is the inverse value of impedance.

The hemodynamic sensor is adapted to generate an output signal that reflects physical activity or hemodynamic need of a patient.

The memory is used for storing data such as data relating to the implantable heart stimulator's operation or physiological data such as an IEGM and intracardiac impedance or data derived from these measurements such as data relating to natural (intrinsic) atrial or ventricular events. An intrinsic event can be a recognized from an intracardiac electrogram since an intrinsic event—an initial contraction of a heart chamber—is initiated by depolarisation of the muscle cells of the heart tissue (myocardium) that leads to electric potential that can be picked up by an intracardiac electrode. The telemetry unit is adapted to allow for wireless transmission of data, e.g. data stored in the memory or data generated or measured by the implantable heart stimulator just in time. Preferably, the telemetry unit is adapted to allow for bidirectional data communication thus enabling remote programming of the implantable heart stimulator.

The control unit is connected to the stimulation pulse generator, the sensing unit, the impedance measuring unit and the hemodynamic sensor and is adapted to determine on a regular basis primary signals including right ventricular unipolar intracardiac impedance values and physical activity values as represented by an output signal of the hemodynamic sensor. The control unit is further adapted to determine from these primary signals one or more of the following indices:

Peak Systolic Dynamics
Resting Systolic Dynamics
Systolic Reserves
Systemic Control Power
Systemic Control Reserves and
Cardiac Demand Balance.

The invention includes the basic idea of using standard statistics obtained by the implantable heart stimulator in combination with the result of intracardiac impedance measurement to characterize and monitor the performance of the heart and the cardiovascular system. It is proposed to monitor, record and analyse primary signals related to cardiac function and systemic vascular function.

These signals include intracardiac electrograms and intracardiac impedance measurement signals. Further signals that can be measured and evaluated include but are not limited to:

subdermal electrograms, transthoracic impedance, transcardiac impedance, thoracic temperature, venous or capillary $O_2$ saturation, acceleration, etc.

The heart stimulator comprises a sensor for each of the signals to be measured. The heart stimulator is preferably adapted to auto adjust each sensor based on the range and distribution of the signal being measured to perform within the sensor's operating range.

The information content of the signals thus derived is to be evaluated and qualified to confirm the demands of the cardiovascular system (metabolic, thermal, stress, etc.) and the internal adjustments by the cardiovascular system (intrinsic adaptation).

The implantable heart stimulator is adapted to generate indices relating to the responsiveness of regulated systems or challenges and to record these indices. The implantable heart stimulator is further adapted to monitor intrinsic adaptation to detect when the cardiovascular system has reached the limits of adaptive reserves.

Preferably, the implantable heart stimulator is adapted to record trends of the signals and the indices derived from these signals, and daily distributions and accumulative distributions of the signals and indices. The implantable heart stimulator further is adapted to make the trends and signals available to the attending health care professional for diagnostic purposes via the telemetry unit.

The implantable heart stimulator further is preferably adapted to receive remote commands via the telemetry unit for setting parameters for the evaluation of signals or the generation of indices. Further, this approach allows an attending health care professional to select indicators to be used for automatic notification. The health care professional may enable and set thresholds related to the signals or indices to trigger alerts and alarms. Triggers can be defined by setting indicators and/or thresholds via remote commands received over the telemetry unit. The implantable heart stimulator preferably is adapted to respond to predefined trigger events (triggers) defined i.e. by thresholds. Depending on the trigger such response may be initiation of a therapy, sending a notification to health care professionals via the telemetry unit or recording more detailed episode information for subsequent review.

One preferred embodiment of the invention is based on the right ventricular and intracardiac impedance signal (RVI), the intracardiac electrogram (IEGM), the cardiac AV sequential rhythms, the lead characteristics and the hemodynamic sensor's output signal.

Preferably the implantable heart stimulator is adapted to maintain daily and weekly trends for the following primary signals:
1) Intrinsic and evoked unipolar intracardiac impedance
2) Intrinsic and evoked P and R wave amplitude
3) Capture threshold (myocardial excitability)
4) Lead resistance and
5) Physical activity as represented by the hemodynamic sensor's output.

The implantable heart stimulator may be adapted to use trends of these primary signals directly and for calculating cardiac and cardiovascular function indices. Further, trends of these primary signals can be used individually or in combination with each other to initiate a transmission of medical alerts via the telemetry unit and the external device to the central service center.

According to the invention, in addition to trends of the primary signals, derived indices are calculated which combine the data available in the primary signals and isolate a cardiac centric performance from systemic specific performance. These indices are derived from the filtered primary signals. The indices are designed to remove interfering and confounding factors using data selection, arithmetic correction, data filtering and normalization.

The many realizations of the derived indices include but are not limited to:
1) Peak Systolic Dynamics,
2) Resting Systolic Dynamics,
3) Systolic Reserves,
4) Systemic Control Power,
5) Systemic Control Reserves, and
6) Cardiac Demand Balance.

Indices 1 through 3 are predominately focused on the heart function, and may be used as measures of cardiac performance. Indices 4 through 6 are predominately focused on the vascular system and may be used as measures of systemic performance.

1) Peak Systolic Dynamics

The Peak Systolic Dynamics represents the maximum strength of the RVI signal, which was sustained for a specified period of time or number of cardiac cycles. The maximum may be defined as the maximum absolute value or the peak-to-peak difference of the RVI measurement associated with a specific cardiac cycle or collection of cardiac cycles. The criterion for achieving the specified duration may be defined as exceeding a threshold value for the specified duration or an average over the specified duration. The Peak Systolic Dynamics may be defined independently for ventricular paced and ventricular sensed events. It may be further sub-classified based on the associated atrial event type and the associated exertion state.

The Peak Systolic Dynamics may be collected and trended on a range of time bases, with temporal resolutions equivalent but not limited to minutes, hours, days and weeks.

2) Resting Systolic Dynamics

The Resting Systolic Dynamic and changes in the Resting Systolic Dynamics reflect the characteristics of the systolic dynamics for specific reproducible conditions. The reproducible conditions may include a specified period of rest, a stable conduction rhythm, a specified posture, and a specified time within the diurnal cycle. Changes in the Resting Systolic Dynamics may be taken with respect to prior measures or a single standard reference condition. By comparing RVI curves obtained under the specified conditions, changes in the Resting Systolic Dynamics may be derived. Change indices may be calculated directly as the average signed or unsigned deviation, or by comparing extracted features of the RVI curves.

The Resting Systolic Dynamics may be defined independently for ventricular paced and ventricular sensed events. It may be further sub-classified based on the associated atrial event type. The Resting Systolic Dynamics may be collected and trended on a range of time bases, with temporal resolutions equivalent but not limited to hours, days and weeks.

3) Systolic Dynamic Reserves—Utilized

The Systolic Dynamic Reserves and changes in the Systolic Dynamic Reserves reflect the capacity of the myocardium to respond to excitatory stimuli and the impedance sensor's ability to measure these changes. The stimulated conditions may include criteria for independent measures of exertion and criteria for a stable cardiac rhythm. Systolic Dynamic Reserves may be calculated from the RVI values collected during the stimulated state and compared to the applicable resting state. The comparative measure may be calculated directly as the average signed or unsigned deviation, or by comparing extracted features of the RVI curves. A peak value for the Systolic Dynamic Reserve may be established over an appropriate observational period.

The Peak Systolic Dynamic Reserves may be defined independently for ventricular paced and ventricular sensed events. It may be further sub-classified based on the associated atrial event type. The Peak Systolic Dynamic Reserves may be collected and trended on a range of time bases, with temporal resolutions equivalent but not limited to days and weeks.

4) Systemic Control Power

The resting Systemic Control Power and changes in the resting Systemic Control Power reflect influences from excitatory and inhibitory control processes on the Systolic Dynamics. The control processes may be neural, humeral or hemodynamic. It includes the capacity of the myocardium to respond to these stimuli and the impedance sensor's ability to measure these responses. The Systemic Control Power reflects the underlying strength, health and status of the systemic regulatory pathways. It may be modulated by chronic and acute events including cardiac medications and diuretics. The basal Systemic Control Power is defined for specific reproducible rest conditions. The reproducible rest conditions may include a specified resting period, a stable conduction rhythm and a specified time within the diurnal cycle. The control power may be defined to be the root mean square power integrated over a frequency band which including one or more of the high frequency, low frequency and very low frequency bands associated with heart variability. The band limited RMS power may be efficiently evaluated as the average of the absolute values of the differences between the outputs of two low pass filters.

The resting Systemic Control Power may be defined independently for ventricular paced and ventricular sensed events. It may be further sub-classified based on the associated atrial event type. The resting Systemic Control Power may be collected and trended on a range of time bases, with temporal resolutions equivalent but not limited to hours, days and weeks.

5) Systemic Control Reserves

The Systemic Control Reserves and changes in the Systemic Control Reserves reflect the capacity of the cardiovascular system to elicit changes in cardiac performance. The cardiac response to systemic control is reflected in the CLS control signal derived from RVI and described in other patents. Systemic Control Reserves may be calculated from the RVI values in a manner similar to the calculation of the rate adaptation. The Systemic Control Reserves is defined as the peak value, which was sustained for a specified period of time or number of cardiac cycles over a specified observational period. The criterion for achieving the specified duration may be defined as exceeding a threshold value for the specified duration or as an average over the specified duration. The Systemic Control Reserves may be defined independently for ventricular paced and ventricular sensed events. It may be further sub-classified based on the associated atrial event type. The Peak Systolic Dynamics may be collected and trended on a range of time bases, with temporal resolutions equivalent but not limited to days and weeks.

6) Systemic Demand Balance—Activities of Daily Living

The Systemic Demand Balance reflects the patient's activities of daily living and the balance between metabolic demands and non-metabolic demands on the cardiovascular system. The Systemic Demand Balance permits the detection of changes in systemic or cardiac performance, which may be secondary to changes in the activities of daily living or physical ability. The Systemic Demand Balance is defined as the time (or cardiac cycles) for which RVI based rate support was provided, and for which there was significant physical exertion. Systemic Demand Balance may be defined over multiple rate intervals spanning the programmed rate adaptive therapy range. Systemic Demand Balance is expressed relative to the total rate support for the applicable rate intervals. The Peak Systolic Dynamics may be collected and trended on a range of time bases, with temporal resolutions equivalent but not limited to days and weeks.

The implantable heart stimulator according to the invention provides for the following advantages:
  It provides detection and records information relating to infrequent systemic circulatory crisis.
  It provides early alert of an acute crisis, thus permitting the timely intervention. (Heart Attacks and Stroke).
  It provides titration monitoring of pharmaceuticals, which have a narrow therapeutic windows.
  It provides cost effective monitoring the progress and efficacy of therapy.
  In the event of a crisis, it allows to guide therapy and diagnosis by providing critical retrospective information.

The features characterizing the implantable heart stimulator according to the invention are not only applicable to pacemakers and defibrillators. They can equally be applied to or be incorporated in other telemedicine products or new monitoring products

BRIEF DESCRIPTION OF THE DRAWINGS

The above and other aspects, features and advantages of the present invention will be more apparent from the following more particular description thereof, presented in conjunction with the following drawings wherein.

DETAILED DESCRIPTION OF THE INVENTION

The following description is of the best mode presently known for carrying out the invention. This description is not to be taken in a limiting sense, but it made for the purpose of describing the general principals of the invention. The scope of the invention should be determined with reference to the claims.

Figure 1:
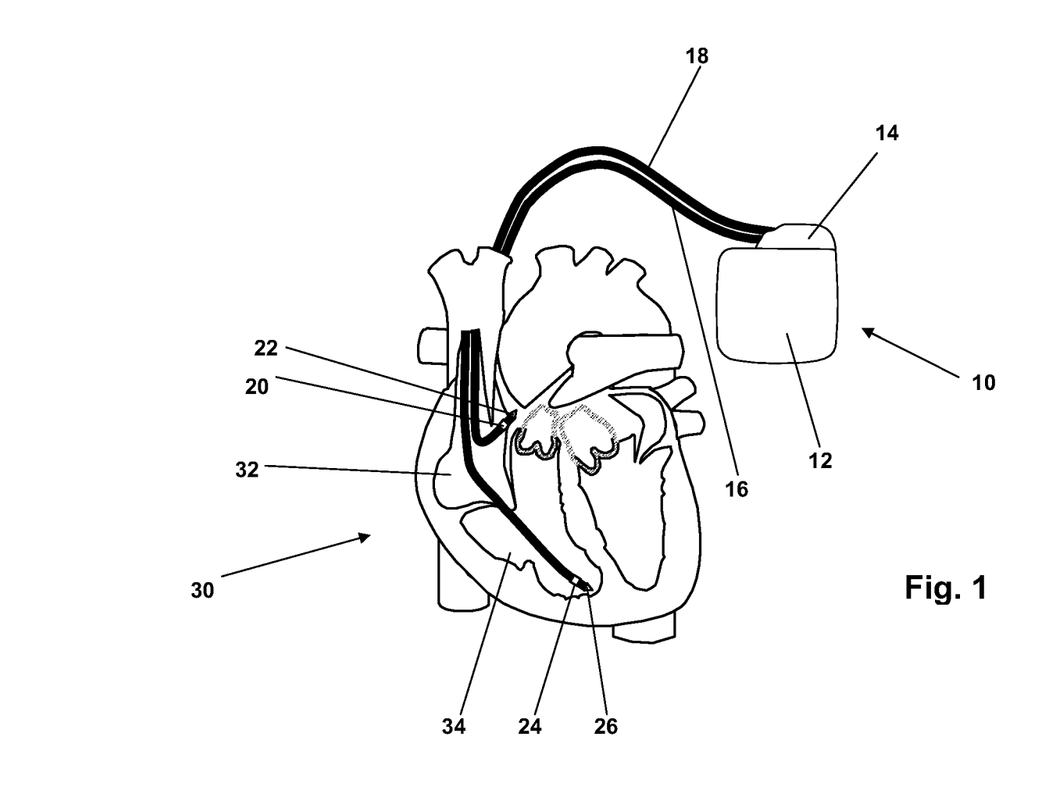
FIG. 1 shows a dual chamber pacemaker connected to leads placed in the heart.

In FIG. 1, a dual chamber pacemaker 10 is illustrated that is connected to a heart by means of pacing/sensing leads 16 and 18.

Pacemaker 10 comprises a housing 12 made from a biocompatible metal such as titanium. Pacemaker 10 comprises a transparent header 14 that is made from electrically insulating plastic and that encloses terminals to which electrode leads 16 and 18 are connected detachably. Electrode leads 16 and 18 each comprise a proximal connector (not shown) that is plugged into the connectors of header 40.

Electrode lead 16 is an atrial electrode lead bearing an atrial tip electrode 22 at its distal end and an atrial ring electrode 20 close to its distal end.

Electrode lead 18 is a ventricular electrode lead bearing a ventricular tip electrode 26 at its distal end and a ventricular ring electrode 24 close to its distal end As it is apparent from FIG. 1, the distal end of atrial electrode lead 16 is placed in atrium 32 of the heart 30, when implanted. The atrial ring electrode 20 and the atrial tip electrode 22 are both placed in the right atrium 32 of the heart 30.

Atrial tip electrode 22 touches the wall of atrium 32 and thus has direct contact to the atrial myocardium.

The distal end of ventricular electrode lead 18 is placed in the right ventricle 34 of the heart 30. Both, the ventricular tip electrode 26 and the ventricular ring electrode 24 are placed in right ventricle 34. The ventricular tip electrode 26 touches the wall of ventricle 34 and thus has direct contact to the myocardium (the heart tissue) of ventricle 34.

Figure 2:
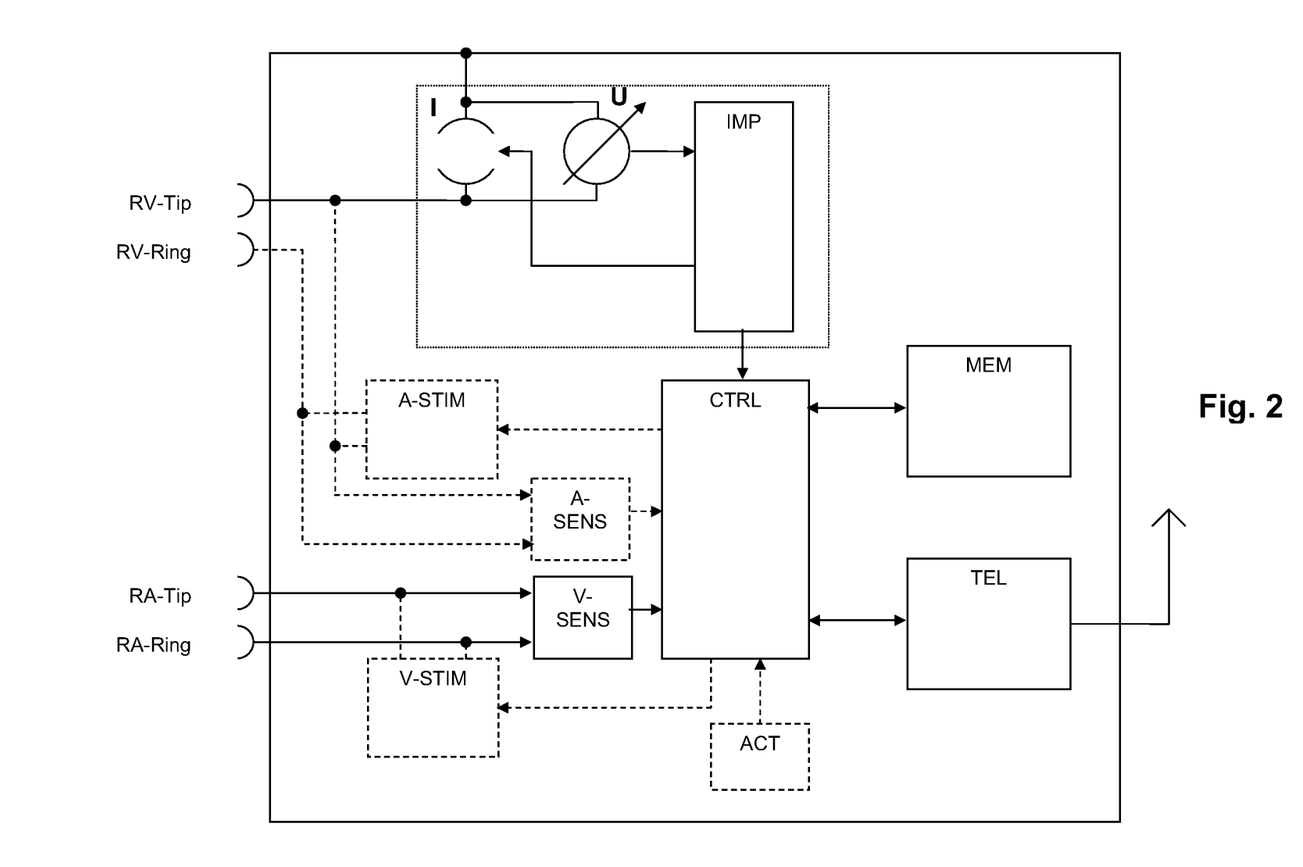
FIG. 2 is a block diagram of the pacemaker of FIG. 1.

The components enclosed in housing 12 are connected via header 14 to electrode leads 16 and 18. In FIG. 2 four terminals are schematically illustrated, a terminal RA ring for the right atrial ring electrode 20, a terminal RA tip for the right atrial ring electrode 22, a terminal RV ring for the right ventricular ring electrode 24 and a terminal RV tip for the right ventricular tip electrode 26.

Terminals AR ring and AR tip are electrically connected to an atrial stimulation unit A-STIM and an atrial sensing unit A-SENS. Thus, electrical potentials picked up in the atrium can be fed to the atrial sensing unit A-SENS to generate an atrial intracardiac electrogram (EGM) as a primary signal. Electrical stimulation pulses can be delivered from the atrial stimulation pulse generator A-STIM via e.g. atrial tip electrode 22 to the myocardium of the right atrium.

Terminals RV-ring and RV-tip are connected to a ventricular stimulation pulse generator V-STIM and a ventricular sensing unit V-SENS. Thus, electrical potentials picked up in the ventricle can be fed to the ventricular sensing unit V-SENS to generate ventricular intracardiac electrogram (EGM) as a primary signal. Ventricular stimulation pulses generated by ventricular stimulation pulse generator V-STIM can be delivered to the right ventricle 34 of the heart 30 via a right ventricular electrode lead 16.

The atrial stimulation pulse generator A-STIM and the atrial sensing unit A-SENS as well as right ventricular stimulation pulse generator V-STIM and the right ventricular sensing unit V-SENS are commonly connected to a control unit CTRL. Control unit CTRL receives the output signals from the atrial sensing unit A-SENS and from the ventricular sensing unit V-SENS. The output signals of sensing units A-SENS and V-SENS are generated each time that a P-wave representing an intrinsic atrial event or an R-wave representing an intrinsic ventricular event, respectively, is detected by evaluating the time course of an intra-atrial EGM or an intraventricular EGM picked up in the right atrium 32 or the right ventricle 34, respectively. An As signal is generated, when the atrial sensing unit A-SENS detects a P-wave and a Vs signal is generated when the ventricular sensing unit V-SENS detects an R-wave.

Atrial and ventricular stimulation pulse generators A-STIM and V-STIM, respectively, are adapted to generate electrical stimulation pulses for pacing a respective heart chamber whenever triggered by control unit CTRL, according to programmed timing regime.

Figure 3:
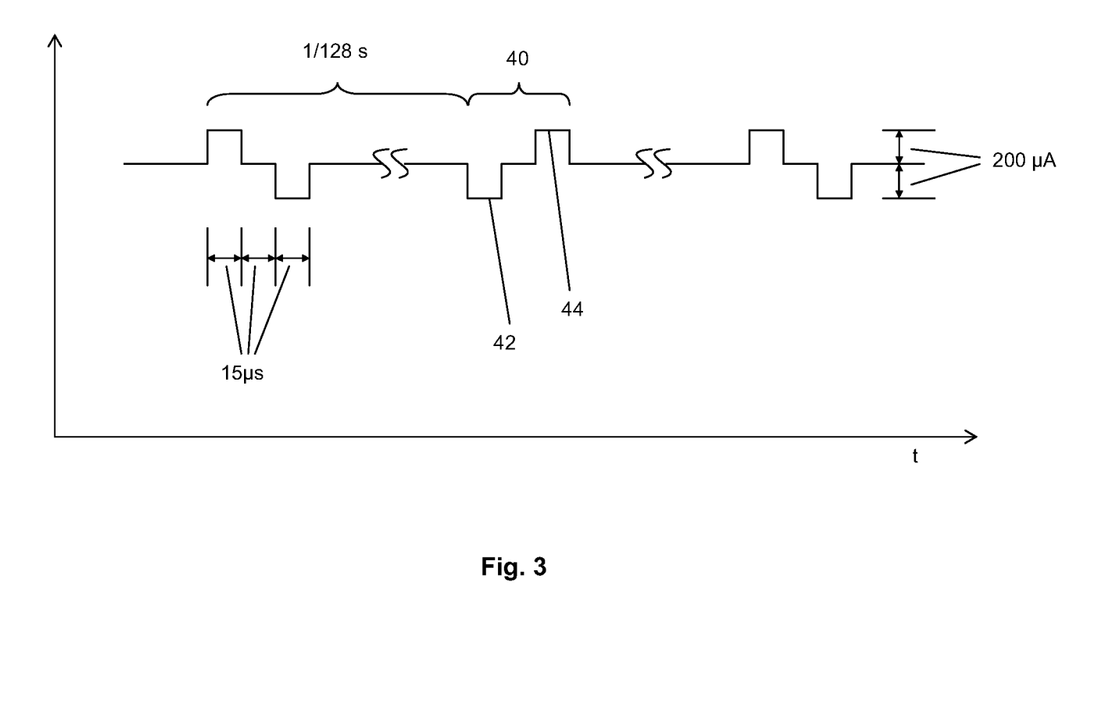
FIG. 3 is a diagram of a polarity sequence of a circuit used for measuring a unipolar intraventricular impedance with the pacemaker of FIGS. 1 and 2.

With respect to one preferred embodiment of the present invention, it is to be noted, that terminal RV-tip is also connected to an impedance measuring unit that comprises a constant current source I, a voltage measuring unit U and an impedance signal generator IMP. The constant current source I and the voltage measurement unit U are also connected to the housing 12 of pacemaker 10 forming a neutral electrode. The impedance signal generator IMP of the impedance measuring unit is adapted to sample a voltage measured by voltage measurement unit U with a sampling rate between 30 Hz and 300 Hz, preferably 128 Hz. In FIG. 3 constant current source I generates a sequence of pairs 40 of constant current pulses with a rate corresponding to the sampling rate. Each pair of constant current pulses comprises two consecutive current pulses 42 and 44 having the same magnitude and duration but different polarity. The polarity sequence of current pulses 42 and 44 of the pairs 40 of current pulses can alternate as it is depicted in FIG. 3.

A preferred sampling rate is 128 Hz. Each pair 40 of constant current pulses preferably has a total duration of 45 µs wherein each constant current pulse has a duration of 15 µs. The two current pulses making one pair of current pulses are spaced in time by 15 µs. The sampling rate, the total duration of pulse pair 40, and the pulse duration are auto adjusted by the control unit CTRL.

The impedance signal thus derived is another primary signal to be further processed by the control unit.

A cardiovascular demand sensor (activity sensor) ACT is provided that generates an output signal reflecting physical activity or hemodynamic need of a patient. A common type of such activity sensor is an accelerometer, e.g. a piezoelectric crystal, mounted to the case of the pacemaker. Other types of cardiovascular demand sensors are also known, such as sensors that sense the oxygen content of blood, respiration rate, blood pH, blood temperature, intra-cardiac impedance changes, and the like. The type of sensor used is not critical to the present invention. Any sensor capable of sensing some physiological parameter relatable to physical activity of a patient can be used. Such sensors are commonly used with "rate-responsive" pacemakers in order to adjust the rate of the pacemaker in a manner that tracks the physiological needs of the patient.

The output signal of the hemodynamic sensor ACT is yet another primary signal to be processed by the control unit.

The control unit CTRL is adapted to process the primary signals and determine from these primary signals one or more of the following indices:

Peak Systolic Dynamics
Resting Systolic Dynamics
Systolic Reserves
Systemic Control Power
Systemic Control Reserves and
Cardiac Demand Balance.

The control unit CTRL is further adapted to extract trends of the signals and the indices derived from these signals, and daily distributions and accumulative distributions of the signals and indices.

The heart stimulator (pacemaker 10) continuously measures the patient's intracardiac ventricular impedance. The control unit extracts cardiac performance information, e.g. the indices, based on the intracardiac impedance, including amplitude, timing and variability of cardiac contraction function. The control unit records and analyses trends in the performance information. The heart stimulator transmits the cardiovascular status via the telemetry unit at regular intervals. The control unit identifies changes, which exceed the set threshold limits. In the event of an incipient crisis as defined by the triggers, the heart stimulator will transmit an alert message via the telemetry unit. On a patient's re-entry into a clinical setting for follow-up, the heart stimulator will automatically provide detailed information on the changes in the cardiovascular performance, the response to treatment, and the disease status.

Further features of the control unit relate to the preferred embodiments of the heart stimulators as mentioned above.

Although an exemplary embodiment of the present invention has been shown and described, it should be apparent to those of ordinary skill that a number of changes and modifications to the invention may be made without departing from the spirit and scope of the invention. In particular, it is possible to implement the invention in other implantable medical devices, such as implantable cardioverters/defibrillators, three chamber biventricular implantable pacemakers for cardiac resynchronization therapy (CRT) or any combination thereof. Thus, the present invention can readily be adapted to a number of different kinds of implantable heart stimulators by following the present teachings. All such changes, modifications and alterations should therefore be recognized as falling within the scope of the present invention.

What is claimed is:

1. An implantable heart stimulator, comprising:
   at least one electrode or at least one connector for electrodes;
   at least one stimulation pulse generator connected to said at least one electrode or said at least one connector for intracardiac placement and configured to
     selectively generate a stimulation pulse for delivery to at least one ventricle of a heart;
   at least one sensing unit connected to said at least one electrode or said at least one connector for intracardiac placement and configured to
     process electric potentials that can be picked up by an intracardiac electrode in said at least one ventricle of said heart to thus acquire an intracardiac electrocardiogram or IEGM;
   at least one impedance measuring unit connected to said at least one electrode or said at least one connector for intracardiac placement and configured to
     determine a unipolar ventricular impedance or conductance signal having a magnitude corresponding to intracardiac impedance of conductivity of said at least one ventricle of said heart;
   a hemodynamic sensor configured to generate an output signal reflecting physical activity or hemodynamic need of a patient;
   a memory unit configured to store data;
   a telemetry unit configured for wireless transmission of data;
   a control unit connected to said at least one stimulation pulse generator, said at least one sensing unit, said at least one impedance measuring unit and said hemodynamic sensor, and configured to
     determine on a regular basis primary signals including ventricular unipolar intracardiac impedance values and physical activity values as represented by an output signal of said hemodynamic sensor; and,
     determine from said regular basis primary signals one or more values of systemic dynamics indices that include:
       Peak Systolic Dynamics,
       Resting Systolic Dynamics,
       Systolic Reserves,
       Systemic Control Power,
       Systemic Control Reserves,
       Cardiac Demand Balance;
     wherein said indices are determined from filtering said regular basis primary signals using a calculation which combines data from said regular basis primary signals and isolates a cardiac centric performance from systemic specific performance; and
     wherein said indices are configured to remove interfering and confounding factors using one or more of data selection, arithmetic correction, data filtering and normalization.

2. The implantable heart stimulator according to claim 1, wherein said peak systolic dynamics values represent a maximum amplitude of a ventricular impedance signal which is sustained for a predetermined period of time or a predetermined number of cardiac cycles as represented by said IEGM.

3. The implantable heart stimulator according to claim 2, wherein said maximum amplitude of said ventricular impedance signal is a maximum absolute value or a peak-to-peak difference of said ventricular impedance signal associated with a specific cardiac cycle or a portion of a cardiac cycle.

4. The implantable heart stimulator according to claim 2, wherein said predetermined period of time or said predetermined number of cardiac cycles is defined as a period of time wherein a threshold impedance value is exceeded, a value of which is configured to optimize state discrimination including but not limited to receiver operating characteristic (ROC) techniques.

5. The implantable heart stimulator according to claim 2, wherein said control unit is configured to determine said peak cardiac systolic dynamics values independently for ventricular paced and ventricular sensed events.

6. The implantable heart stimulator according to claim 2, wherein said control unit is configured to determine said peak systolic dynamics values independently for different types of atrial events associated with the ventricular events.

7. The implantable heart stimulator according to claim 2, wherein said control unit is configured to collect and trend said peak systolic dynamics values based on a range of time bases, with temporal resolutions equivalent but not limited to minutes, hours, days and weeks.

8. The implantable heart stimulator according to claim 1, wherein said resting systolic dynamics values represent a characteristic magnitude or amplitude of a ventricular impedance signal during a predetermined period of low physical activity as represented by an output signal of said hemodynamic sensor.

9. The implantable heart stimulator according to claim 1, wherein said resting systolic dynamics values represent a characteristic magnitude or amplitude of a ventricular impedance signal during a predetermined period of low physical activity as represented by a stable conduction rhythm.

10. The implantable heart stimulator according to claim 1, wherein said resting systolic dynamics values represent a characteristic magnitude or amplitude of a ventricular impedance signal during a predetermined period of low physical activity as represented by a specified posture.

11. The implantable heart stimulator according to claim 1, wherein said resting systolic dynamics values represent a characteristic magnitude or amplitude of a ventricular impedance signal during a predetermined period of low physical activity as represented by a specified time within the diurnal cycle.

12. The implantable heart stimulator according to claim 1, wherein said control unit is configured to determine changes in said resting systolic dynamics values with respect to prior measures of said resting systolic dynamics values or a single standard reference condition.

13. The implantable heart stimulator according to claim 1, wherein said control unit is configured to determine changes in said resting systolic dynamics values by comparing ventricular impedance curves obtained under specified conditions.

14. The implantable heart stimulator according to claim 12, wherein said control unit is configured to directly calculate change indices as an average signed or unsigned deviation of said resting systolic dynamics values from prior measures of said resting systolic cardiac dynamics values or a single standard reference condition.

15. The implantable heart stimulator according to claim 13, wherein said control unit is configured to calculate change indices by comparing extracted features of said ventricular impedance curves.

16. The implantable heart stimulator according to claim 1, wherein said control unit is configured to determine said resting systolic dynamics values independently for ventricular paced and ventricular sensed events.

17. The implantable heart stimulator according to claim 1, wherein said control unit is configured to sub classify said resting systolic dynamics values based on an associated atrial event type.

18. The implantable heart stimulator according to one of claim 1, wherein said control unit is configured to collect and trend said resting systolic dynamics values on a range of time bases, with temporal resolutions equivalent but not limited to hours, days and weeks.

19. The implantable heart stimulator according to claim 1, wherein said systolic reserves values are calculated from a distribution in ventricular impedance signals collected during periods of rest and during periods of activity as indicated by a cardiac demand sensor.

20. The implantable heart stimulator according to claim 19, wherein said control unit is configured to calculate said systolic reserves values from the difference in the medians of the activity and resting distributions divided by the half width of the resting distribution.

21. The implantable heart stimulator according to claim 19, wherein said control unit is configured to calculate said systolic reserves values from distributions of a characteristic magnitude obtained from said ventricular impedance signals.

22. The implantable heart stimulator according to claim 19, wherein said control unit is configured to calculate said systolic reserves values by comparing extracted features of the ventricular impedance curves.

23. The implantable heart stimulator according to claim 19, wherein said control unit is configured to establish a peak value for said systolic reserves values over an appropriate observational period.

24. The implantable heart stimulator according to claim 19, wherein said control unit is configured to determine peak systolic reserves values independently for ventricular paced and ventricular sensed events.

25. The implantable heart stimulator according to claim 19, wherein said control unit is configured to sub-classify said systolic reserves values based on the associated atrial event type.

26. The implantable heart stimulator according to claim 19, wherein said control unit is configured to collect and trend said systolic reserves values on a range of time bases, with temporal resolutions equivalent but not limited to days and weeks.

27. The implantable heart stimulator according to claim 1, wherein said systemic control power values represent a root means square power integrated over a frequency band which includes one or more of high frequency, low frequency and very low frequency bands associated with heart variability wherein said heart variability is configured to be derived from ventricular impedance signals.

28. The implantable heart stimulator according to claim 27, wherein said control unit is configured to determine a basal systemic control power value for specific reproducible rest conditions.

29. The implantable heart stimulator according to claim 28, wherein said specific reproducible rest condition is a specified resting period.

30. The implantable heart stimulator according to claim 28, wherein said specific reproducible rest condition is a stable conduction rhythm and a specified time within the diurnal cycle.

31. The implantable heart stimulator according to claim 27, wherein said control unit is configured to determine a basal systemic control power value as the root mean square power integrated over a frequency band which including one or more of the high frequency, low frequency and very low frequency bands associated with heart rate variability.

32. The implantable heart stimulator according to claim 31, wherein said control unit is configured to determine a band limited root mean square power as an average of absolute values of differences between outputs of two low pass filters.

33. The implantable heart stimulator according to claim 28, wherein said control unit is configured to determine said basal systemic control power value independently for ventricular paced and ventricular sensed events.

34. The implantable heart stimulator according to claim 28, wherein said control unit is configured to sub-classify said basal systemic control power values based on an associated atrial event type.

35. The implantable heart stimulator according to claim 28, wherein said control unit is configured to collect and trend said basal systemic control power values on a range of time bases, with temporal resolutions equivalent but not limited to hours, days and weeks.

36. The implantable heart stimulator according to claim 1, wherein said systemic control reserves value represents a maximum of integral values wherein each integral value is determined for one heart cycle and represents the integrated ventricular impedance signal between a Q-wave and a R-wave in the corresponding IEGM.

37. The implantable heart stimulator according to claim 36, wherein said control unit is configured to calculate said systemic control reserves values from the ventricular IEGM in a manner similar to calculation of rate adaptation.

38. The implantable heart stimulator according to claim 36, wherein said control unit is configured to determine said systemic control reserves values by determining a peak value, which was sustained for a specified period of time or number of cardiac cycles over a specified observational period.

39. The implantable heart stimulator according to claim 38, wherein said specified observational period is defined as exceeding a threshold value for a specified duration or as an average over said specified duration, a value of which is configured to optimize state discrimination including but not limited to receiver operating characteristic (ROC) techniques.

40. The implantable heart stimulator according to claim 36, wherein said control unit is configured to determine said systemic control reserves values independently for ventricular paced and ventricular sensed events.

41. The implantable heart stimulator according to claim 36, wherein said control unit is configured to sub-classify said systemic control reserves values based on an associated atrial event type.

42. The implantable heart stimulator according to claim 36, wherein said control unit is configured to collect and trend said systemic control reserves values on a range of time bases, with temporal resolutions equivalent but not limited to days and weeks.

43. The implantable heart stimulator according to claim 1, wherein said systemic demand balance value represents a ratio between a daily average heart rate elevation during periods of elevated cardiovascular demand and a daily average magnitude of one or more hemodynamic sensors.

44. The implantable heart stimulator according to claim 1, wherein said systemic cardiac demand balance value represents a time period or a number of cardiac cycles for which ventricular impedance based rate support is provided, and for which there is significant physical exertion as indicated by said hemodynamic sensor output signal.

45. The implantable heart stimulator according to claim 44, wherein said control unit is configured to determine said systemic cardiac demand balance value over multiple rate intervals spanning a programmed rate adaptive therapy range.

46. The implantable heart stimulator according to claim 45, wherein said control unit is configured to determine said systemic cardiac demand balance value relative to a total rate support for applicable rate intervals.

47. The implantable heart stimulator according to claim 43, wherein said control unit is configured to collect and trend a plurality of said systemic cardiac demand balance values on a range of time bases, with temporal resolutions equivalent but not limited to days and weeks.

\* \* \* \* \*